(12) United States Patent
Bauer

(10) Patent No.: US 6,221,014 B1
(45) Date of Patent: *Apr. 24, 2001

(54) DEVICE FOR TRACKING THE FOCUS POSITION FOR A THERAPY APPARATUS

(75) Inventor: Edgar Bauer, Kraichtal (DE)

(73) Assignee: Richard Wolf GmbH, Knittlingen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/977,492

(22) Filed: Nov. 24, 1997

(30) Foreign Application Priority Data

Nov. 22, 1996 (DE) .............................. 196 48 338

(51) Int. Cl.$^7$ .................................................. A61B 17/22
(52) U.S. Cl. .............................................. 600/439; 601/4
(58) Field of Search ............................ 601/2–4; 600/439, 600/101, 109, 117, 118, 160, 167, 173; 606/130; 378/62–65, 68, 69, 205; 382/128, 131, 132

(56) References Cited

U.S. PATENT DOCUMENTS

| 4,669,483 | * | 6/1987 | Hepp et al. | 600/439 |
| 4,936,291 | * | 6/1990 | Forssmanne et al. | 600/439 |
| 4,986,275 |  | 1/1991 | Ishida et al. . |  |
| 4,991,604 | * | 2/1991 | Wurster et al. | 600/439 |
| 5,098,426 | * | 3/1992 | Sklar et al. | 606/5 |
| 5,150,712 | * | 9/1992 | Dory | 601/4 |
| 5,158,085 |  | 10/1992 | Belikan et al. . |  |
| 5,165,412 |  | 11/1992 | Okazaki . |  |
| 5,178,135 | * | 1/1993 | Uchiyama et al. | 601/4 |
| 5,269,306 |  | 12/1993 | Warnking et al. . |  |
| 5,301,660 |  | 4/1994 | Rattner . |  |
| 5,315,986 | * | 5/1994 | Lacruche et al. | 600/439 |
| 5,431,621 | * | 7/1995 | Dory | 601/2 |
| 5,506,912 | * | 4/1996 | Nagasaki et al. | 600/103 |
| 5,817,014 | * | 10/1998 | Hori et al. | 600/118 |
| 5,820,545 | * | 10/1998 | Arbter et al. | 600/117 |
| 5,836,869 | * | 11/1998 | Kudo et al. | 600/173 |
| 6,014,473 | * | 1/2000 | Hossack et al. | 382/294 |

FOREIGN PATENT DOCUMENTS

| 35 43 867 | 6/1987 | (DE) . |
| 38 11 872 | 10/1989 | (DE) . |
| 43 00 740 | 3/1994 | (DE) . |
| 419 933 | 4/1991 | (EP) . |

* cited by examiner

Primary Examiner—Brian L. Casler
(74) Attorney, Agent, or Firm—Cohen, Pontani, Lieberman & Pavane

(57) ABSTRACT

There is disclosed a device for tracking a target mark with a diagnosis apparatus, in particular an ultrasound therapy apparatus coupled to a therapy apparatus, in particular to an ultrasound therapy apparatus. A target mark control as a control unit separate from the ultrasound diagnosis apparatus is installed to acquire the relative position of the transmitter/receiver head to the sound source of the ultrasound therapy apparatus as well as different zoom regions of the ultrasound diagnosis apparatus and/or a change of position of the represented ultrasound picture, and to track a target mark represented on a monitor so that this target mark always designates the position of the focus of the sound source. By way of the separation, with respect to the apparatus, of the target mark control from the ultrasound diagnosis apparatus, parameters adapted to differing ultrasound diagnosis apparatus may be inputted into the target mark control for tracking the target mark, this being without changing the hardware or software of the ultrasound diagnosis apparatus or of the ultrasound therapy apparatus. The change in the zoom region or in the position of the monitor picture is preferably acquired on the basis of a change, effected by this, in the picture geometry of the picture represented on the monitor.

7 Claims, 5 Drawing Sheets

DEVICE FOR TRACKING THE FOCUS POSITION FOR A THERAPY APPARATUS

BACKGROUND OF THE INVENTION

The invention relates to a device for tracking the a target mark for a therapy apparatus which in particular serves as an ultrasound therapy apparatus, for example a lithotripter, for the destruction or treatment of objects in the inside of a human or animal body and which is coupled to a diagnosis apparatus, in particular an ultrasound diagnosis apparatus, which comprises an ultrasound transmitter/receiver head, for scanning the object, and which is coupled to a sound source, for example a pressure impulse source, of the ultrasound therapy apparatus, wherein the position of the transmitter/receiver head relative to the axis of symmetry of the sound source can be adjusted and wherein the scanning plane of the transmitter/receiver head goes through the focus of the sound source.

Such a device is known from DE 35 43 867 A1 (Richard Wolf GmbH). The known device serves for the location and destruction of concretions in bodily organs, such as for example kidney stones, and offers a simplified and inexpensive apparatus with regard the design of the structural components, and in which the body organ, the concretion located therein, as well as the destruction procedure may be acquired by the transmitter/receiver head of the ultrasound diagnosis apparatus and may be displayed on a monitor. Subsequently the known device is explained with reference to FIGS. 6 and 7 which schematically show a pressure impulse source or a shock wave transducer 1 in combination with a transmitter-receiver head of an ultrasound diagnosis apparatus.

The shock wave transducer 1 has the shape of a spherical calotte in which individual piezoelectric transducer elements, which are not further represented, are arranged and with their active beaming surface are directed on the focus 2.

With the device according to FIG. 6, the transmitter/receiver head 3 (B-scanner) of the diagnosis apparatus (not shown) is so fixed at the upper end of the holder 4 that the longitudinal axis 5 of the scanner and the axis of symmetry 6 of the shock wave transducer 1 coincide. The holder 4 runs through the centre of the transducer 1 which in a central region 1a does not comprise any transducer elements by which means the holder 4 and the scanner 3 will lie in a sound shadow having the peripheral shape of a cone 7, even when here the scanner or its holder externally protrudes relatively far out of the space enclosed by the spherical calotte shape of the transducer 1.

The outer contour of the shock wave field intersecting at the focus 2 is indicated by the cone 8. A concretion 102 for example in a kidney 101 of the patient 10, and on which the focus 2 in this case is already directed, is to lie in the section plane 9 acquired by the scanner 3 and lying in the plane of the drawing.

Moreover the holder 4 with the scanner 3 may be turned about the axis of symmetry 6 in the direction of the arrow A, this for example being with an angular range of 90°, so that the production of at least two correspondingly angularly displaced sectional pictures is possible. Furthermore the scanner 3 by way of axial movement of the holder 4 relative to the transducer 1 may be adjusted in the direction of the double arrow B, by which means an adaptation of the scanner position to the patient is possible. A further possible position of the holder 4 and of the section plane 9 is shown dashed in FIG. 6.

If the scanner 3 as with the device according to FIG. 6 projects relatively far into the usual sound field geometry of the transducer 1 and thus from the beginning has a correspondingly small distance to the concretion 102, then advantageously a commercially available and thus inexpensive, short focusing scanner may be applied. This advantage in general does not apply to a device according to the type of embodiment shown in FIG. 7, in which the scanner 3 is arranged in or directly bordering the space enclosed by the calotte shape of the transducer 1, and may not be axially adjusted. On the other hand it is advantageous with this embodiment that for the shielding of the scanner and its holder in the centre of the transducer calotte, only a relatively small surface of transducer elements must remain free.

Furthermore also with the device according to FIG. 7, the holder with the scanner 3 in the transducer center is rotatably mounted (arrow A) about the axis of symmetry 6. By way of this, as with the previously described example, the representation of several section planes 9 is possible. Although in FIG. 7 seven various section planes distributed about 360° are drawn in, in practise the representation of for example two section planes displaced by 90° is sufficient and with this an unproblematic location of the concretion is made possible. Furthermore with this device, on the one hand a relatively long focusing B-scanner becomes necessary, but on the other hand, also during the application with shock waves, an ultra-sound control via the scanner is possible since the scanner, after completion of the locating procedure and also during the operation of the transducer 1, may remain in its shown position and continuously produce B-pictures.

Moreover both devices according to FIGS. 6 and 7 fulfill the ideal requirements for locating and destroying body concretions, since the transducer 1 and the B-scanner 3 lie on the same axis 6 and since because of this, the same tissue layers are passed through, from the location sound field as well as from the shock wave sound field. Thus it is usually not possible for various interruptions, possibly caused by imaging errors, of the wave fronts of both sound fields to occur.

Ultrasound diagnosis apparatus and therapy apparatus are principally two apparatus applied for various purposes, which should also be operable independently of one another. This means that with a combination envisaged by this invention of such differing apparatus, it is desirable that various ultrasound diagnosis apparatus, in particular any commercially available ultrasound diagnosis apparatus may be coupled in combination with a therapy apparatus for example, without having to carry out complicated and costly adaptations of both these apparatus.

SUMMARY OF THE INVENTION

The object of the invention thus lies in tracking a produced target mark, which can be displayed on the monitor of the ultrasound diagnosis apparatus under evaluation of the video signal corresponding to various values with respect to the length and/or brightness of picture elements, always on the focus position of the sound source of the ultrasound therapy apparatus, so that the focus position on the monitor, at any time and with differing ultrasound diagnosis apparatus, can be displayed by the target mark and that the target mark should then always be exactly placed on the focus position when the enlargement scale of the applied ultrasound diagnosis apparatus is changed or a sector displacement is effected.

An automatic tracking of a target mark pictured on a monitor is already known from DE 43 00 740 C1. The known apparatus firstly differs from the present basically in that an X-ray source and an X-ray picture receiver is provided in combination with a lithotriptor. On the sound source or the shock wave transducer of the ultrasound therapy apparatus there is arranged a distance recorder which produces a signal with regard to the pivoting position of the transducer. A control device receiving the produced signal, via a memory, has access to data of the actual coordinates of the target mark pictured on the monitor in the end positions of the transducer. On pivoting the ultrasound transducer, of course the focus position of the focus blended into the X-ray picture by an X-ray positive leaded body (e.g. a lead ball) is also co-pivoted on a certain path. The control unit computes, by way of the coordinates of the actual focus position stored in the memory, a path on which the focus travels on pivoting the transducer. The resulting deviations are evaluated and the electronic target mark produced by the target mark generator is correspondingly tracked, so that it may be represented on the monitor at the computed position.

For achieving the above mentioned object the device put forward here is according to one essential aspect of the invention characterized in that the therapy apparatus comprises an electronic position transmitter which yields an electrical position signal indicating the position of the transmitter/receiver head relative to the axis of symmetry of the sound source, and that a control unit is provided which receives the position signal produced by the position transmitter, produces a target mark superimposed on the video signal of the diagnosis apparatus and tracks the position of the target mark depending on the position signal corresponding to the momentary position of the transmitter/receiver head relative to the sound source, and that the control unit further comprises means which acquires a zoom change or a sector displacement of the picture produced by the ultrasound diagnosis apparatus for representation on a monitor and carries out a tracking of the target mark, corresponding to this change, to the current focus position.

BRIEF DESCRIPTION OF THE DRAWINGS

Further advantageous features and problem posing of the invention are hereinafter described in more detail in embodiment examples with reference to the accompanying drawing figures. The figures illustrate individually.

DETAILED DESCRIPTION OF THE INVENTION

Figure 1:
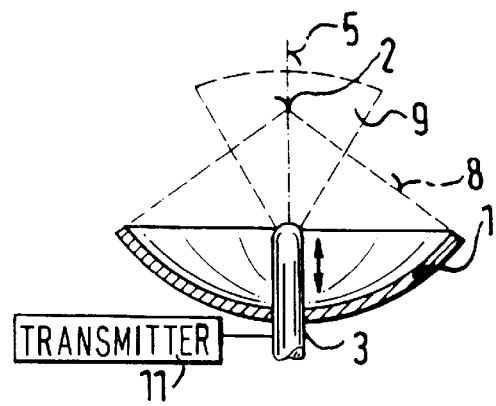
FIG. 1 schematically, a sound source of an ultrasound therapy apparatus in combination with an ultrasound transmitter/receiver head which is displaceable in the axial direction.
Figure 6:
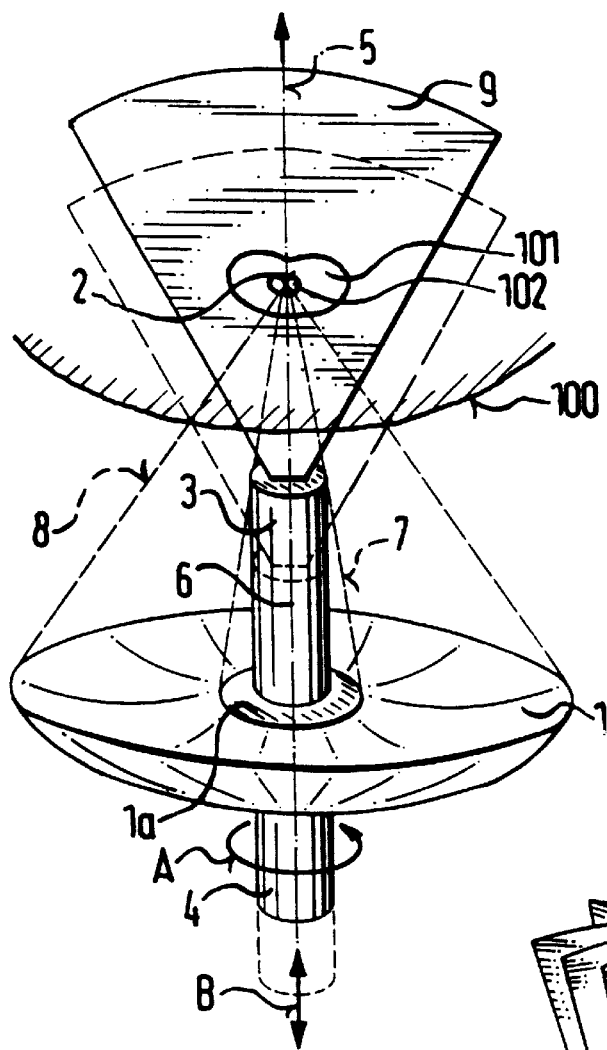
FIGS. 6 and 7 schematic diagrams representative of embodiments of known ultrasound therapy devices.
Figure 7:
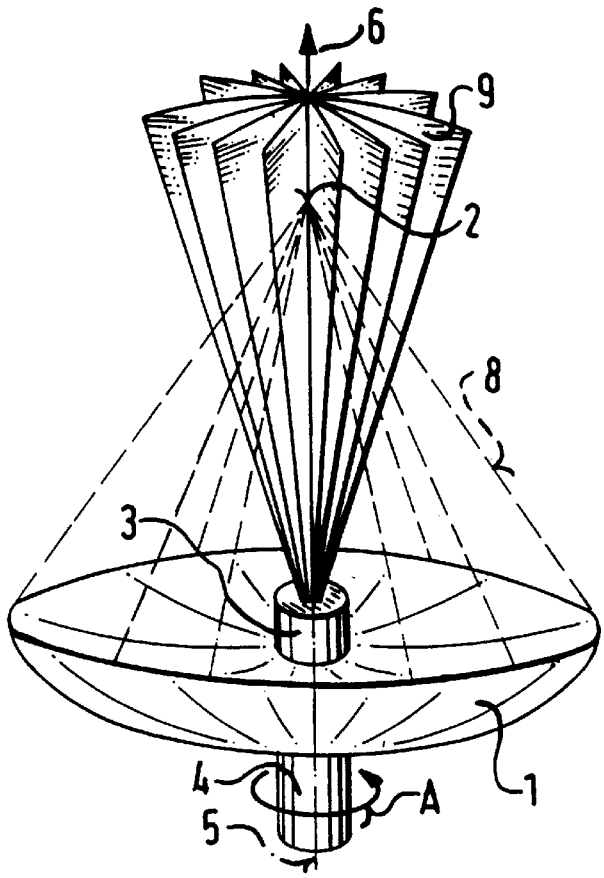

Principally the arrangement, schematically represented in FIG. 1, of the pressure impulse source 1 and of the transmitter/receiver head 3 of the ultrasound therapy apparatus which is not shown in FIG. 1, is the same as is already described in DE 35 43 867 A1 and described above by way of FIGS. 6 and 7. The transmitter/receiver head 3 is upwardly and downwardly displaceable along the axis of symmetry 5. A position transmitter 11 is arranged such that it acquires the actual position of the transmitter/receiver head 3 with respect to the axis of symmetry 5 and produces a corresponding electrical signal. Of course the transmitter/receiver head 3 can also be arranged rotatably about the axis of symmetry 5, as was explained by way of FIG. 7, wherein then the position transmitter 11 is installed as an angle transmitter. Position transmitters for acquiring a linear change in distance as well as for acquiring the angular position are known per se.

Figure 2:
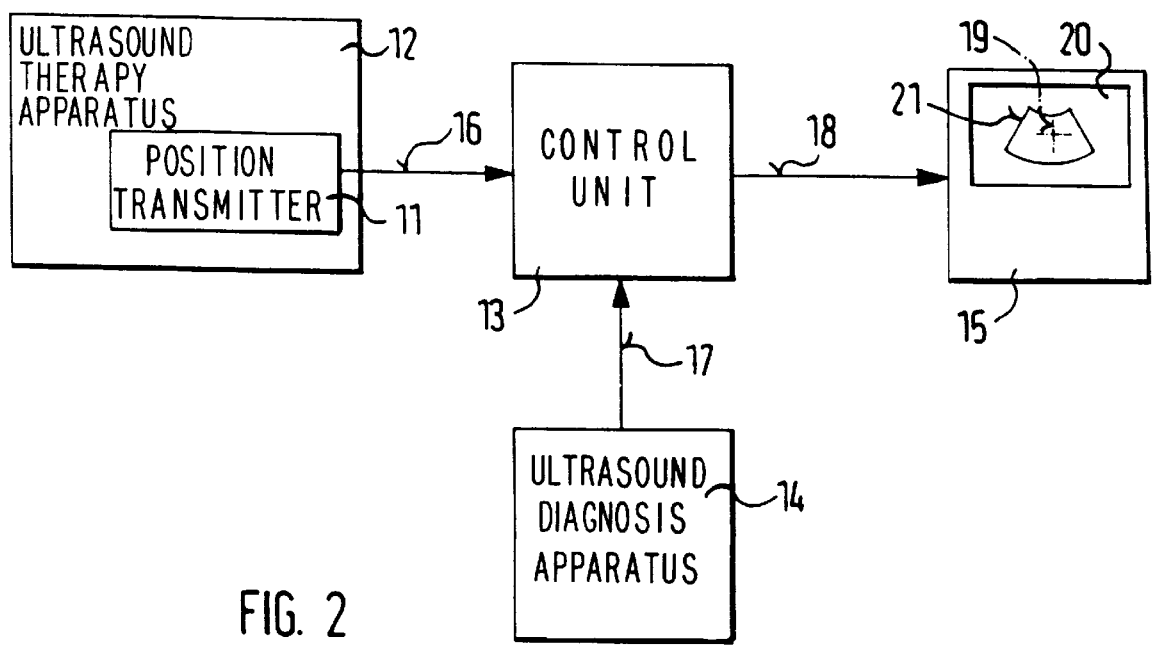
FIG. 2 a block diagram of the device according to the invention.

FIG. 2 represents the essential part of the device according to the invention in the form of a functional block diagram. The position transmitter is allocated to the ultrasound therapy apparatus 12. The position of the transmitter/receiver head 3 acquired by the position transmitter 11, i.e. the scanner position, is supplied in the form of a scanner position signal 16 to a control unit 13 also designated as a TMC (target mark control). The TMC 13 receives from the ultrasound diagnosis apparatus 14 a video signal 17 and mixes this video signal 17 with a target mark which designates the focus position of the sound source 1 or of the ultrasound therapy apparatus 12 and which e.g. can be shown in the form of a target cross 19 on the screen 20 of a monitor 15. The tracking of the target mark 19 corresponding to the position of the transmitter/receiver head and corresponding to the zoom position is described further below in detail.

It is to be noted here that the TMC 13 according to FIG. 2 is realized separately from the ultrasound diagnosis apparatus 14 so that any commercially available ultrasound diagnosis apparatus may be applied. Moreover the TMC 13, as is explained further below in more detail, has at its disposal an input interface as well as a memory for inputting and storing values and signals which take into account the characteristics of the ultrasound diagnosis apparatus 14 applied in each case.

Hereinafter with reference to FIGS. 3 and 4 there is an explanation of the acquisition of the zoom size or position, i.e. of the enlargement scale of the imaging, produced on the monitor, of the video signals of the ultrasound diagnosis apparatus 14. With this the recognition of the enlargement scale by way of the permanent control of the video signal 17 produced by the ultrasound diagnosis apparatus 14 and supplied in a line manner to the TMC 13 is effected.

Figure 4A:
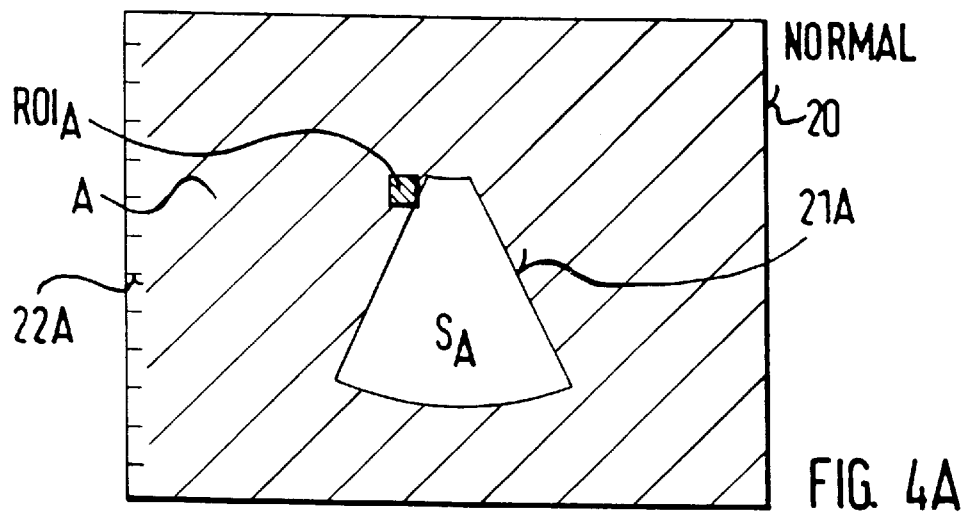
FIGS. 4A, B and C schematically, three resulting sector-like pictures of an ultrasound diagnosis apparatus at three different zoom positions.
Figure 4B:
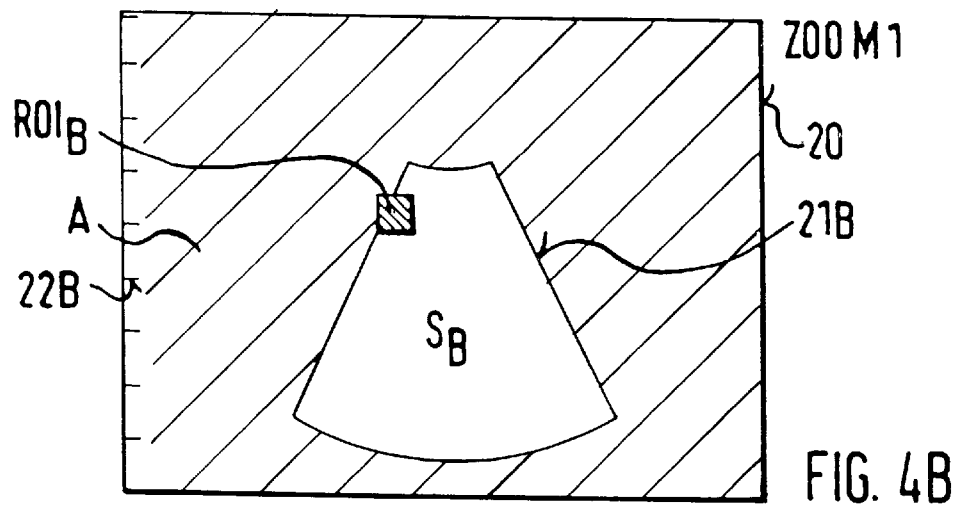
Figure 4C:
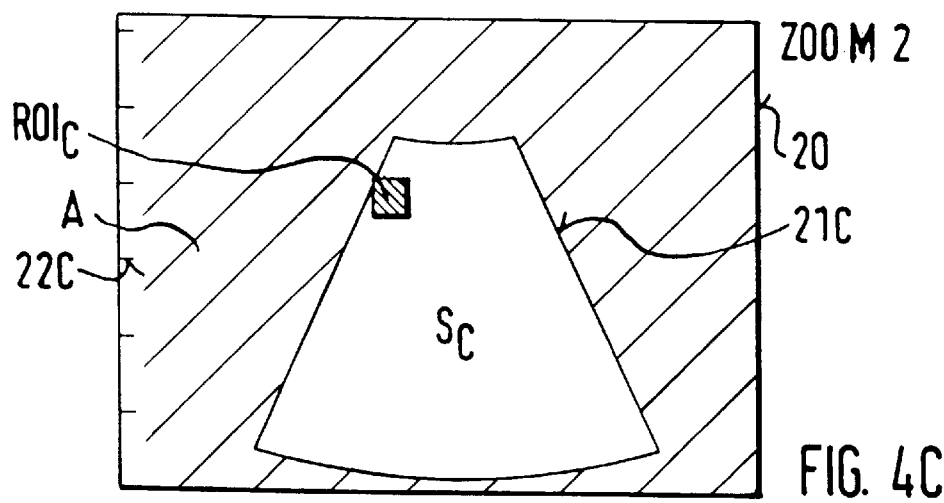

If with the ultrasound diagnosis apparatus 14 another zoom region is chosen, the picture geometry on the monitor correspondingly changes, as is shown by way of FIGS. 4A, 4B and 4C. In the representation produced on the screen 20 of the monitor 15, the region A without picture information (black monitor region) may be exactly delimited from the region S with picture information ($S_A$, $S_B$, $S_C$ according to three differing zoom regions). Thus also an enlargement or reduction of the imaging region of the ultrasound diagnosis apparatus 14 formed by the sector $S_A$, $S_B$, $S_C$ may be evaluated and then the target cross position may be corrected, corresponding to the zoom region.

Figure 3:
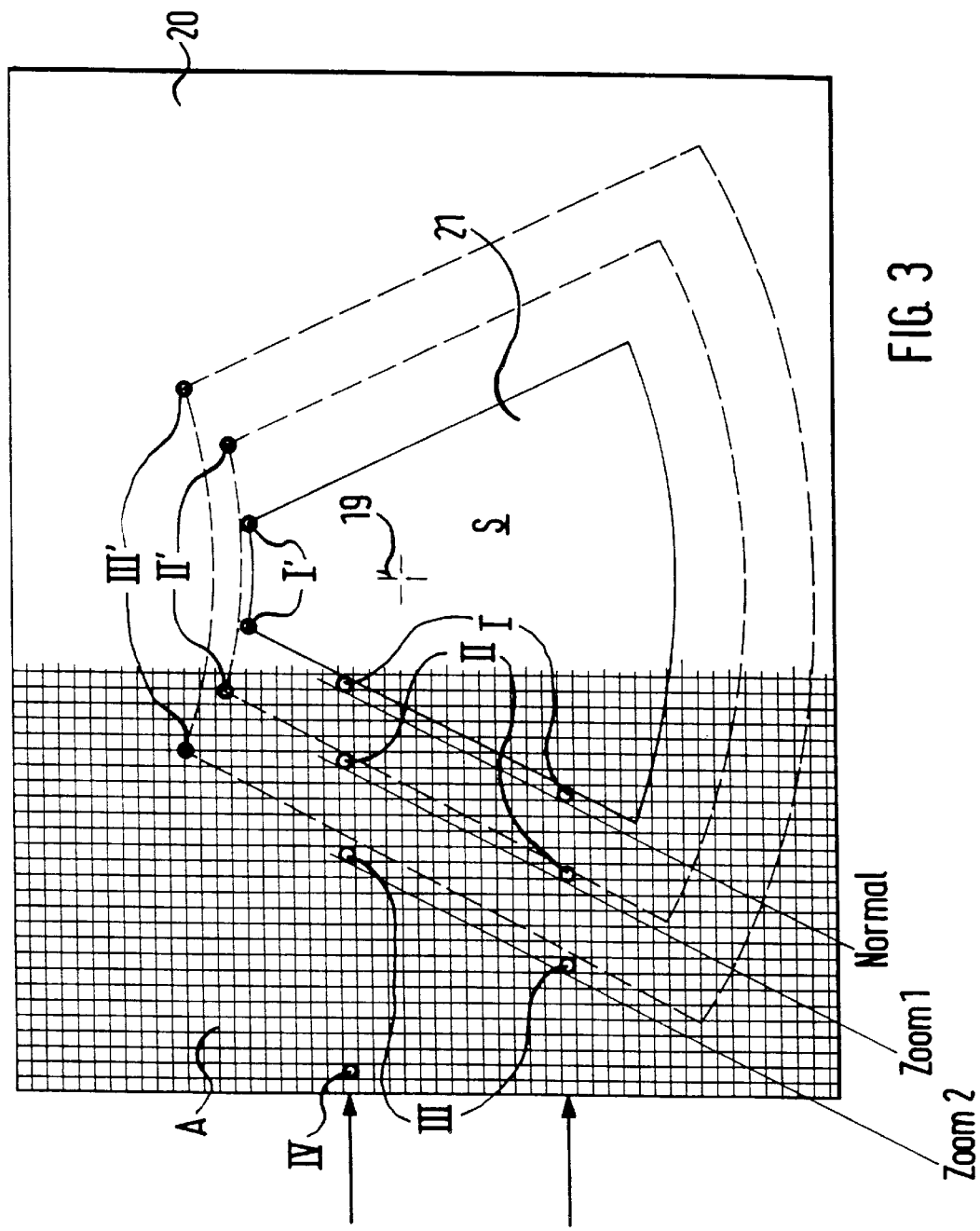
FIG. 3 schematically, a sector-like picture of an ultrasound diagnosis apparatus represented on the monitor screen with a target mark at three various zoom positions for explaining the function of the adaptation to the zoom position.

A preferred realization of the recognition of the zoom region in each case is explained by way of FIG. 3. In order to unambiguously and securely recognize the transition from region A to region S, at least two elements at the beginning of sector S should be controlled. This means that for each zoom region two picture elements are fixed which then serve as thresholds as to whether the zoom region is not exceeded or is exceeded. In FIG. 3 the picture element IV serves as a reference picture element for the picture brightness set. By way of a comparison of the brightness value of picture element IV with the picture element pairs I, II and III, the decision is made as to whether the normal enlargement scale, the zoom region 1 or the zoom region 2 is activated.

If for example it results that the brightness value of the picture element pair I is equal to the brightness value of the comparison picture element IV, then the normal enlargement region is activated; if on the other hand the brightness value of the picture element pair II is equal to the brightness value of the comparison element IV and the brightness value of the picture element pair I is however not equal to that of the comparison element IV, then the zoom region I is activated etc. With further picture element pairs, e.g. I', II' and III', or by way of a corresponding placing of the picture element pairs I, II and III at the beginning/end of the sector, then as additional information it may be deduced whether a sector is displaced within the monitor pictures.

Figure 5:
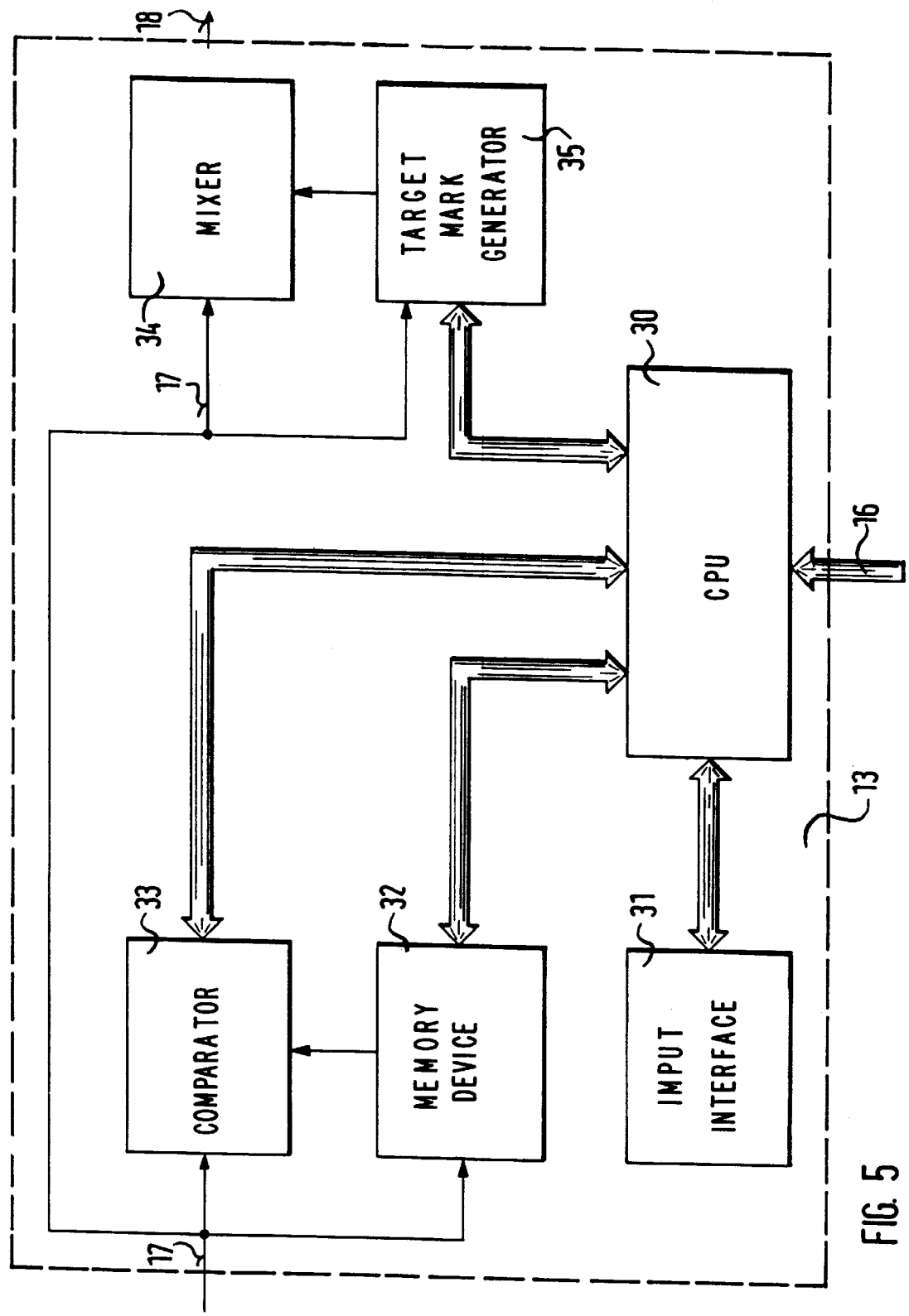
FIG. 5 a block diagram of the target mark control unit 13 according to FIG. 2.

The procedure carried out for this in the TMC 13 is described by way of the block diagram in FIG. 5.

FIG. 5 shows a block diagram of the TMC 13 according to the invention. Via an input interface 31 the individual zoom limits or the position of the sector picture for the applied ultrasound diagnosis apparatus 14 are inputted and are stored in a memory device 32 via a CPU 30. The video signal 17 of the ultrasound diagnosis apparatus 14 arriving at the video input of the TMC 13, at the selected picture element pairs I, II, III, is compared with the values deposited in the memory 32 with respect to their brightness value or compared with the brightness value of the comparison element IV and therefrom the zoom size is computed and then the position of the target mark 19 e.g. a target cross, produced by the target mark generator 35 is correspondingly tracked.

Likewise from the position transmitter 11 the CPU 30 receives the current value for the adjusted height of the ultrasound scanner or of the transmitter/receiver head 3 of the ultrasound diagnosis apparatus 14 and computes from this current value, together with the result from the comparator 33, the current target cross position. The target mark produced by the target mark generator 35 in the form of a reticule is superimposed on the video signal 17 with the help of a mixer 34.

Thus the CPU 30 computes and controls the position of the target mark mixed with the video signal 17 corresponding to the output values of the position transmitter 11 and of the comparator 33 so that the position of the target mark always indicates the current focus position of the sound source 1.

Hereinafter by way of FIGS. 4A, B and C still alternative methods for evaluating the zoom sizes are described.

Alternatively the enlargement scale or the zoom size of the ultrasound diagnosis apparatus may also be recognized in that a window region (ROI=Region of Interest) is defined such that the window region ROI given a normal enlargement scale lies completely outside of the sector $S_A$, given a zoom size 1 lies partly outside and partly within sector $S_B$, and given a zoom size 2 lies completely within sector $S_C$ (FIGS. 4A, B, C).

Finally a further possibility of recognition of the enlargement region or the zoom position lies in depositing the distances of the scalings 22A–C in the memory device 32 of the TMC 13. As FIGS. 4A–C show, the distance of the scale parts of the scales 22A, 22B and 22C (measuring ruler) changes on transition to another enlargement so that the enlargement or zoom region, by way of a constant comparison of the stored distance values with a value indicating the distance of the scale parts of the current picture in each case, may be recognized.

Because for various ultrasound diagnosis apparatus 14 the region limits between the extremely dark region A without picture information and the region S containing the picture information of the ultrasound diagnosis apparatus run differently, and also because the distances of the measuring scale 22 or the brightness and position of the scale parts at the edge of the monitor screen may be different, the CPU 13 may store corresponding data inputted via the presetting input interface 31 in the memory 32 and use this data for recognizing the respective zoom region and finally for tracking the target mark. Changes at the ultrasound diagnosis apparatus 14 are thus not required since the TMC is realized separately.

The subject-matter of the invention, as has already been described earlier by way of preferred embodiment forms, is a device which can control or regulate a target mark for a therapy apparatus, e.g. a lithotriptor, a hypothermia apparatus or a therapy apparatus for treating bones or soft tissue with sound waves and for example with a pressure impulse source as a sound source, the therapy apparatus beings so coupled to a commercially available ultrasound diagnosis apparatus that the sound source of the ultrasound therapy apparatus is combined with the transmitter/receiver head (B-scanner) for scanning the object, wherein the position of the transmitter/receiver head relative to the axis of symmetry of the sound source is so adjustable that the scanning plane always goes through the focus of the sound source. This device is characterized in that the therapy apparatus comprises an electronic position transmitter which yields an electrical signal indicating the position of the transmitter/receiver head relative to the axis symmetry of the sound source, that there is provided a control unit separate from the ultrasound diagnosis apparatus and designated TMC, which receives the position signal, produces a target mark superimposed on the video signal of the diagnosis apparatus and tracks the position of the target mark, dependent on the position signal, corresponding to the momentary position of the transmitter head relative to the sound source, and that this TMC further comprises means which acquires a zoom change of the picture produced by the ultrasound diagnosis apparatus and carries out a tracking, of the target mark to the current focus position, corresponding to the change in zoom setting or the sector position (sector displacement).

The advantages of the device according to the invention are in particular:

Any commercially available ultrasound diagnosis apparatus can be coupled to the ultrasound therapy apparatus without complicated and costly changes in its hardware and software.

The TMC which is provided separately from the ultrasound diagnosis apparatus, permits the input and memory of parameters taking into account the characteristics of the respective ultrasound diagnosis apparatus for recognition of the position of the transmitter/receiver head of the ultrasound diagnosis apparatus as well as for the recognition of the zoom setting and sector position, so that also with the use of differing ultrasound diagnosis apparatus the target mark always exactly represents the focus of the therapy apparatus. Adaptations, with respect to apparatus, of hardware and software of the ultrasound therapy apparatus as well as of the ultrasound diagnosis apparatus to one another may be done away with. The implementation of the TMC essentially by way of hardware and software components of a commercially available microprocessor is simple and flexible and thus is inexpensive for the user.

Also with X-ray apparatus there is the possibility of selecting various zoom sizes. Herewith however, the active picture surface is not altered but only the picture content is altered, i.e. represented larger or smaller. In order to be able to evaluate the zoom size a measuring object must be brought into the active picture, which may for example be achieved in that an X-ray positive, thus an X-ray opaque material with a certain shape, for example a metal platelet, is brought into the beam path between the image intensifier and X-ray irradiator. This metal platelet appears on the X-ray picture as a dark rectangle and with an enlargement of a picture is enlarged and with a reduction is reduced. Thus by way of a measuring object which is defined in the size and shape and which is arranged at a fixed point in the beam path of the X-ray apparatus, then the current zoom setting may be evaluated by way of the change in object visible on the monitor.

What is claimed is:

1. An apparatus for tracking a target mark for a therapy device for providing therapy to an object in a patient's body via a sound source positioned at a focus position corresponding to a location of the object, the sound source having an axis of symmetry, the therapy device being coupled to an ultrasound diagnosis apparatus having a display screen and a scanning unit for scanning the object of the therapy device in a scanning plane, wherein in any position of the scanning unit relative to the axis of symmetry, the scanning plane intersects the focus position, and wherein the ultrasound diagnosis apparatus generates a video signal representative of an image of the object in the scanning plane for display on the display screen, which image has a plurality of portions, the apparatus comprising:

tracking means for generating a first signal representative of a position of the scanning unit relative to the axis of symmetry; and control means, operatively coupled to said tracking means, for:

receiving said first signal, generating from the video signal a second signal representative of at least one of a current zoom setting and a current sector displacement of the image generated by the ultrasound diagnosis apparatus, and determining a desired coordinate position of a target mark image in accordance with said first and second signals, such that said coordinate position of said target mark image corresponds to the focus position, the control means including means for determining one of a change in the zoom setting and a sector displacement of the image displayed on the display screen, and for tracking the target mark to the current focus position based on this change.

2. The apparatus of claim 1, wherein said control means further comprises:

sensing means, for determining said current zoom setting of the image in accordance with a change in a picture geometry of the image from the picture geometry of a previous zoom setting.

3. The apparatus of claim 1, wherein said control means further comprises:

defining means for defining a window region of the image, first sensing means for determining a current brightness characteristic value for a portion of the image within said window region;

second sensing means for determining said current zoom setting of the image by comparing said current brightness characteristic value to a predefined expected brightness characteristic value.

4. The apparatus of claim 3, wherein said control means further comprises:

input means for defining a plurality of zoom settings corresponding to the ultrasound diagnosis apparatus; and memory means for storing said plurality of zoom settings.

5. The apparatus of claim 4, wherein said input means further comprises means for defining a different expected brightness characteristic value for said window region corresponding to each zoom setting of said plurality of zoom settings, and wherein said memory means further comprises means for storing said expected brightness characteristic values for each corresponding zoom setting.

6. The apparatus of claim 1, wherein said control means further comprises means for storing coordinates of a nominal focus position of the therapy apparatus and for storing coordinates representative of a plurality of positions of the scanning unit that are furthest from the focus position.

7. The apparatus of claim 1, wherein said control means comprises a microprocessor and wherein tracking of the focus position is performed in accordance with a control program executed by said microprocessor.

* * * * *